United States Patent
Soito et al.

(10) Patent No.: US 6,673,024 B2
(45) Date of Patent: Jan. 6, 2004

(54) CYTOLOGICAL EVALUATION OF BREAST DUCT EPITHELIAL CELLS RETRIEVED BY DUCTAL LAVAGE

(76) Inventors: Angela Soito, 230 Commons La., Foster City, CA (US) 94404; Britt-Marie Ljung, 3837 Clay St., San Francisco, CA (US) 94115; Karen Chew, 116 CSM Dr., San Mateo, CA (US) 94402

( * ) Notice: Subject to any disclaimer, the term of this patent is extended or adjusted under 35 U.S.C. 154(b) by 0 days.

(21) Appl. No.: 09/916,647

(22) Filed: Jul. 30, 2001

(65) Prior Publication Data

US 2002/0058887 A1 May 16, 2002

Related U.S. Application Data

(60) Provisional application No. 60/221,864, filed on Jul. 28, 2000.

(51) Int. Cl.[7] ................................................. A61B 5/00
(52) U.S. Cl. ........................... 600/573; 600/584; 604/28
(58) Field of Search ................................. 600/562, 563, 600/573, 576, 584; 435/40.5, 40.51, 6, 7.1, 7.23; 604/28, 22

(56) References Cited

U.S. PATENT DOCUMENTS

| | | | |
|---|---|---|---|
| 3,786,801 A | * | 1/1974 | Satorius ..................... 128/2 F |
| 5,169,774 A | | 12/1992 | Frankel et al. |
| 6,137,899 A | * | 10/2000 | Lee et al. .................... 382/133 |
| 6,413,228 B1 | * | 7/2002 | Hung et al. .................. 600/562 |
| 6,494,859 B2 | * | 12/2002 | Love et al. .................... 604/28 |

OTHER PUBLICATIONS

Jin, Zhang et al, Study of Tumor Markers in Mammary Ductal Lavage for Early Dection of Breast Carcinoma, I, Chinese Tumor Clinical Medicine, vol. 23, Issue 6, pp. 381–385, 1996 (with English Translation attached).

Sartorius, Breast Fluid Cells Help In Early Cancer Detection, JAMA, vol. 224(6), pp 823–827, 1973.

Papanicolaou et al, "Exfoliative Cytology of the Human Mammary Gland and Its Value in the Diagnosis of Cancer and Other Diseases of the Breast", Cancer, pp 377–409, Mar./Apr., 1958.

Petrakis, "Physiological, biochemical, and cytological aspects of nipple aspirate fluid", Breast Cancer Research and Treatment, vol. 8, pp 7–19, 1986.

Petrakis, "Studies on the epidemiology and natural history of benign breast disease and breast cancer using nipple aspirate fluid", Cancer Epidemiology, Biomarkers and Prevention, vol. 2, pp 3–10, Jan./Feb. 1993.

Petrakis, "Nipple Aspirate Fluid in Epidemiological Studies of Breast Disease", Ekpidemiologic Reviews, vol. 15, pp 188–195, 1993.

Sauter et al, "Nipple aspirate fluid: a promising non–invasive method to identify cellular markers of breast cancer risk", British Journal of Cancer, vol. 76(4), pp 494–501, 1997.

Imayama et al, Cancer, vol. 78, pp 1229–1234, 1996.

Love & Barsky, Breast–duct endoscopy to study stages of cancerous breast disease, Lancet, vol. 348, pp 997–999, 1996.

Goodson WH & King EB, Chapter 4: Discharges and Secretions of the Nipple, The Breast: Comprehensive Management of Benign and Malignant Diseases, 2nd Ed., vol. 2, Bland & Kirby eds. W.B. Saunders Co., Philadelphia, PA, pp 51–74, 1998.

(List continued on next page.)

Primary Examiner—Charles Marmor
(74) Attorney, Agent, or Firm—Banner & Witcoff, Ltd.

(57) ABSTRACT

Methods and systems for cytologically evaluating breast duct epithelial cells retrieved by ductal lavage by morphology and other parameters.

22 Claims, 1 Drawing Sheet

OTHER PUBLICATIONS

Wrensch et al, Breast Cancer Incidence in Women with Abnormal Cytology in Nipple Aspirates of Breast Fluid, American Journal of Epidemiology, vol. 135 (2), pp 130–41, 1992.

Wrench et al. Breast Cancer Research and Treatment, "Factors associated with obtaining nipple aspirate fluid: Analysis of 1428 women and literature review", vol. 15, pp 39–51, 1990 Sauter et al, Prostate–Specific Antigen Levels in Nipple Aspirate Fluid Correlate with Breast Cancer Risk, Cancer Epidemiology, Biomarkers & Prevention, vol. 5(12), pp 967–70, 1996.

Wrensch et al, Breast Fluid Cholesterol and Cholesterol B–Epoxide Concentrations in Women with Benign Breast Disease, Cancer Res., vol. 49, pp 2168–2174, 1989.

King et al, Nipple Aspirate Cytology for the Study of Breast Cancer Precursors, JNCL, vol. 71(6), pp 1115–1121, 1983.

Sartorius et al, Cytologic Evaluation of Breast Fluid in the Detection of Breast Disease, J. Natl Cancer Inst, vol. 59, pp 1073–1080, 1977.

Fryberg and Masood Copeland EM 3d. Bland Kl., (*Ductal carcinorna* in situ of the breast) Surgery, Gynecology & Obstetrics, vol. 177(4), pp 425–40, 1993.

King et al, Cytometry, "Analytic Studies of Foam Cells From Breast Cancer Precursors", vol. 5, pp 124–130, 1984.

King et al, A.J.C.P., "Cellular Composition of the Nipple Aspirate Specimen of Breast Fluid", vol. 64, pp 728–738, 1975.

Masood et al, The Missing Link: A "Pap Smear" For Early Breast Cancer Detection and Prevention, The Breast Journal, vol. 5, pp 1–2, 1999.

Petrakis et al, Studies on the Epidemiology and Natural History of Benign Breast Disease and Breast Cancer Using Nipple Aspirate Fluid, Cancer Epidemiology, Biomarkers and Prevention, vol. 2, pp 3–10, 1993.

Sartorius et al, Cytologic Evaluation of Breast Fluid in the Detection of Breast Disease, NCI, vol. 59, pp 1073–1080, 1977.

Fabian et al, J. Cellular Biochemistry, Biomarker and Cytologic Abnormalities in Women at High and Low Risk for Breast Cancer, vol. 17G, pp 153–160, 1993.

Porter–Jordan and Lippman, "Overview of the biological markers of breast cancer", Hematology/Oncology Clincs of North America, vol. 8(1), pp 73–100, 1994.

Sauter et al, Prostate–Specific Antigen Levels in Nipple Aspirate Fluid Correlate with Breast Cancer Risk, Cancer Epidemiology, Biomarkers & Prevention, vol. 5(12), pp 967–70, 1996.

Sartorius, O.W. et al., "Cytologic Evaluation Of Breast Fluid In The Detection Of Breast Disease", Journal Of The National Cancer Institute, vol. 59, No. 4, pp 1073–1080, 1977.

King, E. B, et al, "Analytic Studies Of Foam Cells From Breast Cancer Precursors", Cytometry, vol. 5, No. 2, pp 124–130, 1984.

Sneige, Nour et al., "Fine needle aspiration cytology of ductal hyperplasia with and without atypia and *ductal carcinoma* in situ", Human Pathology, vol. 25, No. 5, pp 485–492, 1994.

Love, Suan M. et al, "Breast–duct endoscopy to study stages of cancerous breast disease", Lancet (North American Edition), vol. 348, No. 9033, pp 997–999, 1996.

King, E. B. et al, Cellular Composition Of The Nipple Aspirate Specimen Of Breast Fluid Part 1 The Benign Cells, American Journal of Clinical Pathology, vol. 64, No. 6, pp 728–738, 1975.

Porter–Jordan, Kathleen et al, "Overview of the biologic markers of breast cancer", Hematology–Oncology Clinics of North America, vol. 8, No. 1, pp 73–100, 1994.

Evron, Ella et al, "Detection of breast cancer cells in ductal lavage fluid by methylation–specific PCR", Lancet (North American Edition), vol. 357, No. 9265, 2001.

\* cited by examiner

CYTOLOGICAL EVALUATION OF BREAST DUCT EPITHELIAL CELLS RETRIEVED BY DUCTAL LAVAGE

Benefit of the Jul. 28, 2000, filing date of the provisional Serial No. 60/221,864 by the same inventors and entitled "Cytological Evaluation of Breast Duct Epithelial Cells" is hereby claimed.

BACKGROUND OF THE INVENTION

1. Field of the Invention

The field of this invention is evaluating human breast duct epithelial cells by cytology to identify breast cancer and breast precancer.

2. Description of the Background Art

Breast cancer is believed to originate in the lining of a single breast milk duct in the breast; and additionally human breasts are believed to contain from 6 to 9 of these ducts. See Sartorius, *JAMA* 224 (6): 823–827 (1973). For several decades significant members of the medical community dedicated to studying breast cancer have believed and shown that the cytological analysis of cells retrieved from nipple discharge from the breast milk ducts can provide valuable information leading to identifying patients at risk for breast cancer. Indeed, Papanicolaou contributed to the genesis of such a possibility of a "Pap" smear for breast cancer by analyzing the cells contained in nipple discharge. See Papanicolaou et al, "Exfoliative Cytology of the Human Mammary Gland and Its Value in the Diagnosis of Cancer and Other Diseases of the Breast" Cancer (1958) March/April 377–409. See also Petrakis, "Physiological, biochemical, and cytological aspects of nipple aspirate fluid", *Breast Cancer Research and Treatment* 1986; 8:7–19; Petrakis, "Studies on the epidemiology and natural history of benign breast disease and breast cancer using nipple aspirate fluid" *Cancer Epidemiology, Biomarkers and Prevention* (January/February 1993) 2:3–10; Petrakis, "Nipple Aspirate Fluid in epidemiological studies of breast disease", *Epidemiologic Reviews* (1993) 15:188–195. More recently, markers have also been detected in nipple fluid. See Sauter et al, "Nipple aspirate fluid: a promising non-invasive method to identify cellular markers of breast cancer risk", *British Journal of Cancer* 76(4):494–501 (1997). The detection of CEA in fluids obtained by a nipple blot is described in Imayama et al. (1996) *Cancer* 78: 1229–1234.

Despite a long history of nipple aspirate fluid and corresponding cytology, questions have remained about the validity and use of nipple aspirate cytology either for making a diagnosis of breast cancer or breast precancer, or for the correlative value of nipple aspirate fluid cytology to histological and pathological readings from a tissue sample or fine needle aspirate (FNA) cytological readings of the same breast.

Random fine needle aspiration (FNA) of breast tissue has been used to detect lesions in the breast, Fabian et al, *J Cell Biochem Suppl* 1997; 28–29: 101–10, using cytological analysis of material retrieved from breast by fine needle aspiration. Sample from FNA can be evaluated by a uniform scheme as detailed in *Amer. J. Surg*, 1997; 174:371–385. FNA as preformed on the breast has several drawbacks. Usually several punctures with an aspiration needle are needed to locate a target lesion; tracks are created with the withdrawal of cancerous cells through the breast with a coordinate risk of spreading the cancer cells to the blood stream along the tracks; scarring can occur at the sites of entry; the punctures can be painful; multiple punctures can result in a sore breast for a time after the procedure; often multiple entries are needed to locate a lesion that provides a positive sample.

Otto Sartorius starting about the mid-1970s obtained some amount of ductal fluid. He accomplished this using a hair thin catheter to infuse saline in the duct, removing the catheter and squeezing the breast or aspirating the nipple surface to get small fluid amounts from the surface. Ductal "washings" have also been reporter by Susan Love in Love & Barsky, (1996) *Lancet* 348: 997–999. Susan Love used a catheter to infuse fluid into a breast duct, then removed the catheter after infusing about 1.5 ml of saline, and collected resulting expressed fluid by squeezing the breast and collecting the "washings" from the nipple surface with a capillary tube.

So described previous attempts at obtaining ductal fluid including nipple aspiration at the nipple surface, either with or without first infusing fluid into the duct, and early attempts at obtaining fluid oozing from the nipple surface after removing the fluid infusion catheter from the duct post fluid infusion have been found inadequate to obtain sufficient cellular yields for a cytological analysis. These samples were not found to be a consistent, uniform, and respected diagnostic tool of breast cancer. Such cytological results, so obtained, have remained ancillary and supportive of other diagnosis (e.g. such as FNA, histology by biopsy, lumpectomy or mastectomy, mammography) and have not been respected as diagnostic information that can stand alone.

The deficiencies of previous nipple aspirate fluid cytology can be mainly attributed to the fact that cellular yields of nipple aspirate fluid are much lower than ductal lavage cell yields when ductal lavage is performed and fluid is retrieved with an indwelling catheter. Petrakis reports that in his studies of some thousands of women over a 20 year study that his average cell yield is about 100 cells per breast, and often less than that using one of the above-mentioned techniques. In a recent clinical trial of about 500 women on whom nipple aspirate fluid was collected prior to ductal lavage with an indwelling catheter, the median number of ductal epithelial cells collected by nipple aspiration was about 120 cells per breast. In addition, samples collected by nipple aspiration tend to yield individual cells, and aggregates or groups of cells of less than 10 cells per aggregate, often less than 5 cells per aggregate, where such groups are collected. Likewise cell yields from these methods using a catheter for fluid infusion of about 1.5 ml of wash fluid, and where the catheter is withdrawn prior to collection of any expressed fluid on the nipple surface, have not yielded cell counts much improved from traditional nipple aspiration.

In contrast, cell yields from ductal lavage samples from infusion of total fluid amounts greater than 2 ml of wash fluid per duct, often greater than 5 ml of wash fluid, commonly as much as in the range from about 10 ml to about 50 ml of wash fluid, and in some cases greater than 50 ml of wash fluid during a lavage procedure on one breast duct where the cells and wash fluid collected are collected while the catheter remains in place in the duct during the procedure have been often greater than 500 cells, commonly from 1000 to 10,000 cells per breast duct, or more per breast duct. In the first trial conducted of its kind with 500 women using a ductal access tool for ductal lavage that permitted infusion of fluid into the breast duct and collection of the fluid mixed with cells while the tool remained in the duct, the mean number of ductal epithelial cells retrieved by ductal lavage was about 40,000 cells/duct and the median number of cells retrieved was about 13,500 cells/duct.

In addition, the cells retrieved by ductal lavage using the methodology of infusion of fluid volumes greater than about 2 ml of saline (e.g. up to about 50 ml or more of fluid during the entire lavage procedure on single duct) and retrieval of the ductal fluid through the lumen of an indwelling catheter, resulted in not only more and larger clumps or clusters of cells, but larger numbers of cells per clump or cluster. Typically, and previously, nipple aspiration yielded clusters or clumps of less than 5 cells per cluster (when clusters are retrieved) and ductal lavage yields clusters or clumps of 10 or more cells per cluster or clump, and substantial numbers of these clumps or clusters. The advantage to cytological readings of clumps or clusters is that they give a cytologist yet another desirable context for relationships between the cells. This context can provide advantages similar to the context derived from a histological analysis where the cells remain in the architecture of the original tissue. The potential for frequent retrieval of cell clumps greater than about 5 cells per clump, especially greater than 10 cells per clump, is a phenomenon not seen in ductal epithelial cell cytology before the ductal lavage techniques so described had been perfected.

In addition, another difference between cells retrieved by ductal lavage and cells retrieved by FNA should be mentioned. Cells retrieved by FNA can include blood from in an around the accessed lesion and can generally be thought of a non-sloughed cells or cells that have not been sloughed from the lesion but rather have been retrieved from a punctured lesion, whereas cells retrieved by ductal lavage (indeed any cells retrieved from the ductal fluid without rupture of the breast tissue, including nipple aspiration, ductal washing collection and ductal lavage) retrieve cells sloughed into the ductal fluid, which cells have left the lesion resident in the breast duct to enter the ductal fluid and be available for retrieval from that fluid source and not from the architecture of the lesion itself as with histology of a biopsy sample or tissue resection and to a lesser extent FNA which retrieves from a lesion but in a more disruptive fashion.

Accordingly, it would be desirable to establish a set of cytological criteria that utilizes, legitimizes and maximizes the new information achievable by newly developed ductal lavage techniques in order to achieve diagnoses of breast cancer and breast precancer that can stand alone and receive acceptance in the medical community without the need for diagnosis from tissue disruption and its coordinate disadvantages.

SUMMARY OF THE INVENTION

The invention provides a method of cytologically evaluating epithelial cells collected from a human breast duct, by providing a ductal fluid sample comprising ductal epithelial cells retrieved by ductal lavage of a duct of a breast of a patient, evaluating the ductal epithelial cells in the sample for one or more indicia selected from the group consisting of cell grouping, cell shape, cell size, nuclear size, nuclear shape, presence or absence of nucleoli, nuclear-to-cytoplasmic ratio, vacuoles in the cytoplasm, cytoplasmic shape, cytoplasmic border, presence or absence of anisonucleosis, presence or absence of mitotic figures, nuclear membrane quality, presence of necrotic debris, chromatin distribution, coarseness of chromatin, and the presence or absence of microcalcifications; and classifying the sample as being normal, atypical or malignant based on the observed indicia.

The sample is classified as malignant when the sample is characterized by at least some of an identifying feature selected from the group consisting of a loss of cell cohesiveness, loose clusters of epithelial cells, enlarged cells, enlarged nuclei, high nuclear-to-cytoplasmic ratio, increased cytoplasm in some cells, irregular nuclear membranes, clumped chromatin, hyperchromatic chromatin, unevenly dispersed chromatin, enlarged nucleoli, multiple nucleoli, marked variation among the cells of the sample in cell size and nuclear size, necrotic debris, and microcalcifications in background material appearing as dense material with smooth borders and concentric layers or dystrophic and amorphous.

The sample is classified as atypical with marked changes when the sample is characterized by at least some of an identifying feature selected from the group consisting of enlarged ductal epithelial cells, marked nuclear increase in ductal epithelial cells, variation in size and shape of the ductal epithelial cells as compared to normal ductal epithelial cells, abundant cytoplasm in some cells, decreased nuclear-to-cytoplasmic ratios in some cells, coarse chromatin, mild abnormality in chromatin distribution, larger nucleoli than in normal cells, multiple nucleoli, more prominent nucleoli, nuclei groups that appear to be overlapping, and mitotic figures.

The sample is classified as atypical with mild changes when the sample is characterized by at least some of an identifying feature selected from the group consisting of single ductal cells, cohesive multilayered cells, complex groups of cells, monolayered cells, an increased number of cell layers compared to normal cells, increased overlapping of the cells, nuclear crowding of cells, minimally enlarged cells, moderate increase in nuclear size to within a range from about 12 to about 16 $\mu$m in diameter, slight anisonucleosis in some cells, and presence of nucleoli.

The sample is classified as normal when the sample is characterized by at least some of an identifying feature selected from the group consisting of single cells, monolayer sheets, tight cells clusters usually one or two cell layers thick, small nuclei in a size range from about 8 to about 12 $\mu$m in diameter, high nuclear-to-cytoplasmic ratio depending on the orientation of the cells in clusters, in single cells a columnar shape of cytoplasm, in single cells discreet small vacuoles in the cytoplasm, in single cells discreet cytoplasmic border, cohesive groups of ductal epithelial cells with cells of uniform size and regular round to oval shape, monolayer sheets of cells with uniform, small cells, monolayer sheets of cells with small inconspicuous nucleoli.

The sample is classified as insufficient cells to make a diagnosis (ICMD) when the sample is characterized by less than 10 epithelial cells in the sample.

The ductal fluid can be retrieved by placing a ductal access tool in the duct and infusing fluid into the duct through the tool and retrieving from the accessed duct through the tool a portion of the infused fluid mixed with ductal fluid that comprises ductal epithelial cells. The method can be repeated for more than one duct on a breast, for a plurality of ducts on a breast. Providing the ductal fluid sample can comprise obtaining the sample from the breast, or receiving a sample which had been previously obtained. The fluid can be obtained by nipple aspiration of the milk ducts.

The fluid sample can be obtained by washing the ductal lumen and retrieving fluid and cells from the lumen. Fluid so obtained can be collected from a single duct, or collected from a plurality of ducts.

The fluid infused can be in a range from about 2 ml to about 100 ml during a total lavage procedure on a single breast duct; the fluid sample retrieved is in a range from about 2ml to about 30 ml of wash fluid mixed with cellular material. The cells retrieved can comprise excess of about 500 cells; the cells retrieved can comprise an amount in a range from about 500 cells to about 40,000 cells from a single breast duct. The sample retrieved can comprise one or more clusters or clumps of cells, wherein a cluster comprises 10 or more ductal epithelial cells.

The method of cytologically evaluating cells collected from a human breast duct can further comprise examining the ductal fluid sample to determine the presence of a marker selected from the group consisting of protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules.

The invention further provides a system of cytological evaluation of epithelial cells collected from a human breast duct comprising: a tool or apparatus for collecting breast duct fluid from a human breast; a chart or written guidelines for evaluating the ductal epithelial cells in the sample for one or more indicia selected from the group consisting of cell grouping, cell shape, cell size, nuclear size, nuclear shape, presence or absence of nucleoli, nuclear-to-cytoplasmic ratio, vacuoles in the cytoplasm, cytoplasmic shape, cytoplasmic border, presence or absence of anisonucleosis, presence or absence of mitotic figures, nuclear membrane quality, presence of necrotic debris, chromatin distribution, coarseness of chromatin, and the presence or absence of microcalcifications; and an algorithm for classifying the sample as being normal, atypical or malignant based on the observed indicia.

The tool or apparatus can comprise a breast duct access fluid and cell retrieval tool, and one or more of a probe, a tool for administering anesthetic, marking tools for marking an accessed or fluid yielding duct or a collection receptacle for the retrieved fluid and cells.

DETAILED DESCRIPTION OF PREFERRED EMBODIMENTS OF THE INVENTION

The following preferred embodiments and examples are offered by way of illustration and not by way of limitation.

Figure 1:
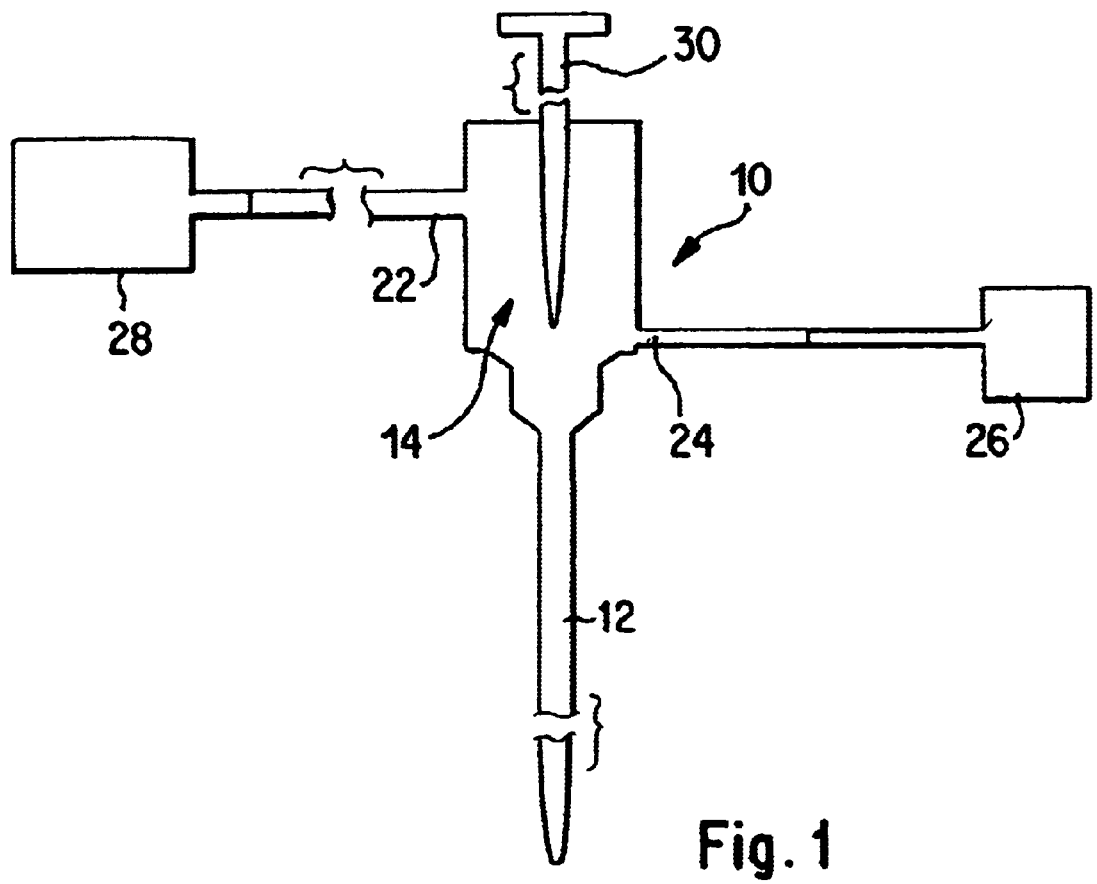
FIG. 1 illustrates a tool for accessing a breast duct according to the present invention.

FIG. 1 illustrates an example of a tool or apparatus 10 for accessing a breast duct and collecting breast duct fluid according to an aspect of the present invention. The tool 10 comprises an elongated single lumen 12 for positioning within the breast duct and infusing and collecting fluid from within the breast duct. The tool 10 also includes a fluid infusion and collection hub 14 that is in fluid communication with the lumen 12. The hub 14 includes an infusion port 24 through which fluid from reservoir 26 is introduced into the hub 14, the lumen 12 and eventually the breast duct. The hub 14 also comprises a collection port 22 which is connected to a collection receptacle 28. Reservoir 26 and receptacle 28 can each comprise a syringe or other well known fluid carrying container. A probe 30 can be used to introduce the lumen 12 into the breast duct or locate a ductal opening.

Figure 2:
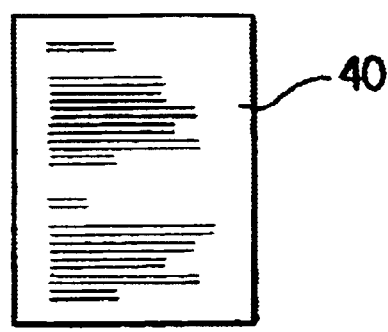
FIG. 2 illustrates a chart according to the present invention.

A chart or written guidelines 40 for evaluating ductal epithelial cells collected from the breast duct is illustrated in FIG. 2.

The invention also provides a method of cytologically evaluating a ductal fluid sample from a human breast to determine whether the sample indicates a normal, atypical or malignant condition in the sampled breast duct. Generally the sample will be retrieved by ductal lavage of a breast duct, however, the invention is not limited to this method of cellular retrieval, provided that the retrieval method yields in excess of about 200 ductal epithelial cells. Samples retrieved by means other than ductal lavage may alternatively comprise 100 ductal epithelial cells or more per breast duct and further comprise one or more ductal epithelial clumps where a clump comprises 10 or more ductal epithelial cells. Thus, for example, other techniques of nipple aspiration that yield enough cells and/or large enough clumps may yield ductal epithelial cells samples sufficient for application of the cytological analysis guidelines provided by the present invention.

However, one aspect of the method of the present invention comprises providing a ductal fluid sample comprising ductal epithelial cells from at least one duct of a breast of a patient wherein the ductal fluid sample is provided by ductal lavage techniques using an indwelling ductal access tool. Providing the ductal fluid sample can comprise obtaining the sample from the breast, or receiving a sample that had been previously obtained. For example, a laboratory can receive a ductal fluid sample from a patient or a practitioner, and the laboratory can be directed to make an analysis of the sample. Where the fluid is obtained from the breast, the fluid sample can be obtained e.g. by nipple aspiration of the milk ducts or by ductal lavage of at least one breast milk duct. When fluid is collected by ductal lavage, the fluid can be collected from a single duct. For example the duct and the collection tube can be marked so that the analysis of the fluid is traceable to one duct.

By the procedure of ductal lavage, ductal epithelial cells that line the walls of the ductal lumen are washed out of the duct. Lavage or wash fluid is infused into the duct, and the lavage fluid mixed with ductal fluid is collected. Infused lavage fluid volumes for the lavage of a single breast duct will be in the range from about 2 ml of wash fluid to about 50 ml of wash fluid, and sometimes in excess of 50 mls of wash fluid depending on the size of the breast of the patient, the size of the accessed breast duct, and the length of time of the procedure. It is generally known that the infused wash fluid, especially if the fluid comprises saline or the like, can diffuse through the ductal wall rather quickly. Wash fluid and cellular material collected for the lavage of a single breast duct will generally be more than 2 ml of wash fluid and cells, often more than 5 mls, and commonly in a range from about 6 ml to about 50 ml of fluid. Most commonly the fluid collected is in a range from about 10 ml to about 30 ml of collected fluid and cells. Breast duct lavage is described in copending and co-owned applications including U.S. Ser. No. 09/067,661, U.S. Ser. No. 09/301,058, PCT US99/09141, U.S. Ser. No. 09/313,463, U.S. Ser. No. 09/473,510, and U.S. Ser. No. 09/506,477 all incorporated by reference in their entirety. In some cases suction can be applied to the tool accessing the ductal lumen in order to retrieve a maximum amount of cells and/or fluid. Lavage or wash fluid can be infused into the duct, and collected. Suction can be applied to the tool accessing the ductal lumen in order to retrieve a maximum amount of cells and/or fluid. Squeezing and other manipulations of the breast to maximize fluid and cellular yield may also be incorporated into the lavage procedure.

Nipple aspiration of breast ductal fluid is achieved by using vacuum pressure. Nipple aspiration techniques are also described and claimed in co-pending and co-owned patent application U.S. Ser. No. 09/438,219, herein incorporated by reference in its entirety. Nipple aspirate fluid can be retrieved as described in e.g. Goodson W H & King E B, *Chapter 4: Discharges and Secretions of the Nipple,* The Breast: Comprehensive Management of Benign and Malignant Diseases (1998) 2$^{nd}$ Ed. vol 2, Bland & Kirby eds. W. B. Saunders Co, Philadelphia, Pa. pp. 51–74; Wrensch et al., (1992) American Journal of Epidemiology. 135(2):130–41; and Sauter et al (1997) British Journal of Cancer. 76(4):494–501. Cells of the lesion can be retrieved by collecting the ductal fluid that contains some of these cells, e.g. by aspirating the nipple to obtain nipple aspirate fluid, e.g. as described in Petrakis (1993) *Cancer Epidem. Biomarker Prev.* 2:3–10, Petrakis (1986) *Breast Cancer Res. Treat* 8: 7–19, Wrensch et al (1992) *Am. J. Epidem.* 135:130–141, Wrensch et al (1990) *Breast Cancer Res Treat* 15: 39–21, and Wrensch et al (1989) *Cancer Res.* 49: 2168–2174. Also fluid secretions from the nipple can be collected as they spontaneously appear on the nipple surface. In order to collect the fluid not mixed with ductal fluid from other ducts, a practitioner carefully watches for the signs of fluid and retrieves the fluid from the nipple surface near the orifice before it has a chance to mix with fluid from any other orifice.

The ductal epithelial cells can be derived from any part of the breast milk duct, including, e.g. the ductal lumen and/or the terminal ductal lobular unit (TDLU). Cells derived from the TDLU may also have similar stages as found in other lumenal ductal epithelial cells not from the TDLU including, e.g. hyperplasia, atypia, in situ carcinoma, and invasive carcinoma; and also the category terms such as normal, mild atypia, marked atypia, and malignant, can be applied equally to these cells from these sources.

The ductal fluid can be retrieved by placing a ductal access tool in the duct and infusing fluid into the duct through the tool and retrieving from the accessed duct through the tool a portion of the infused fluid mixed with ductal fluid. The process may be repeated for more than one duct on a breast, and/or the process can be repeated for a plurality of ducts on a breast. Either sequential or simultaneous access of the duct on a breast can be used. Ductal lavage will generally result in retrieval of sufficient cell samples in excess of 100 ductal epithelial cells, often in a range from about 100 to about 1000 ductal epithelial cells, commonly in a range from about 1000 to 10,000 ductal epithelial cells, and not infrequently samples in excess of 10,000 ductal epithelial cells, and not uncommonly cell samples in a range from about 15,000 to about 20,000 ductal epithelial cells per accessed breast duct. Where a sample results in a cell yield of about 100 ductal epithelial cells, either by ductal lavage or nipple aspiration on the nipple surface, sufficient samples for application of the cytological analysis described herein need further comprise at least one cell clump comprising 10 or more ductal epithelial cells in the clump for the analysis to fit within the parameters and assurances provided herein.

The cells retrieved or collected from the breast duct are evaluated for indicia of cancer or precancer using cytology. The ductal epithelial cells in the sample are evaluated for one or more indicia selected from the group consisting of cell grouping, cell shape, cell size, nuclear size, nuclear shape, presence or absence of nucleoli, nuclear-to-cytoplasmic ratio, vacuoles in the cytoplasm, cytoplasmic shape, cytoplasmic border, presence or absence of anisonucleosis, presence or absence of mitotic figures, nuclear membrane quality, presence of necrotic debris, chromatin distribution, coarseness of chromatin, and the presence or absence of microcalcifications. Based on the presence of any one or more of the observable indicia listed, the sample is then classified as being normal (or benign), atypical (including either mild or marked atypia) or malignant. Table I below indicates additional details for applying the indicia above in order to classify the cells.

TABLE I

| Criteria | Benign Features | Atypical Features | Malignant Features |
|---|---|---|---|
| Epithelial Cell Size (including cytoplasm) | Normal | Moderately enlarged | Enlarged |
| Nuclear Size | Normal (8–12 $\mu$m) | Moderate increase (12–16 $\mu$m) | Marked increase (>16 $\mu$m) |
| Cell Arrangement | Monolayer, single cells or small cohesive clusters no more than 2 cell layers thick or 3-D clusters | Small groups or 3-D varying size clusters which may be >2 cell layers thick; may be significant number of single cells, may have nuclear overlap, papillary structures and be irregularly arranged | Loss of cohesiveness (single cells with or without varying size clusters, cluster may be mutilayered and/or irregularly arranged) |
| Microcalcifications | Usually absent | May be present | May be present |
| Anisonucleosis | Absent or mild | Moderate | Conspicuous |
| Nuclear Membrane | Regular and smooth | Moderate irregularity | Marked irregularity |
| Chromatin | Fine granules, evenly dispersed | Coarse granules, mild abnormality of distribution | Clumped, hyperchromatic, unevenly dispersed |
| Nucleoli | Absent (may be present but small and inconspicuous) | Small and inconspicuous, or may be large | Large and conspicuous, significant number of nucleoli |
| Mitoses | Usually absent | May be present | May be present |
| Multinucleation | Usually absent | May be present | May be present |
| Necrotic Debris | Absent | Possible/some degeneration | May be present - particularly in high grade lesions |

TABLE I-continued

| Criteria | Benign Features | Atypical Features | Malignant Features |
| --- | --- | --- | --- |
| N/C ratio | Within normal limits | May show moderate increase, often variable | May show marked increase, often variable |

A malignant sample is characterized by at least one of the following: loss of cell cohesiveness, loose clusters of epithelial cells, enlarged cells, enlarged nuclei, high nuclear-to-cytoplasmic ratio, increased cytoplasm in some cells, irregular nuclear membranes, clumped chromatin, hyperchromatic chromatin, unevenly dispersed chromatin, enlarged nucleoli, multiple nucleoli, marked variation among the cells of the sample in cell size and nuclear size, necrotic debris, or microcalcifications in background material appearing as dense material with smooth borders and concentric layers or dystrophic and amorphous.

Marked atypia is characterized by at least one of the following: enlarged ductal epithelial cells, marked nuclear increase in ductal epithelial cells, variation in size and shape of the ductal epithelial cells as compared to normal ductal epithelial cells, abundant cytoplasm in some cells, decreased nuclear-to-cytoplasmic ratios in some cells, coarse chromatin, mild abnormality in chromatin distribution, larger nucleoli than in normal cells, multiple nucleoli, more prominent nucleoli, nuclei groups that appear to be overlapping, and mitotic figures.

Mild atypia is characterized by at least some of the following: single ductal cells, cohesive multilayered cells, complex groups of cells, monolayered cells, an increased number of cell layers compared to normal cells, increased overlapping of the cells, nuclear crowding of cells, minimally enlarged cells, moderate increase in nuclear size to within a range from about 12 to about 16 µm in diameter, slight anisonucleosis in some cells, and presence of nucleoli.

Normal or benign conditions are characterized by at least one of single cells, monolayer sheets, tight cells clusters usually one or two cell layers thick, small nuclei in a size range from about 8 to about 12 µm in diameter, high nuclear-to-cytoplasmic ratio depending on the orientation of the cells in clusters, in single cells a columnar shape of cytoplasm, in single cells discreet small vacuoles in the cytoplasm, in single cells discreet cytoplasmic border, cohesive groups of ductal epithelial cells with cells of uniform size and regular round to oval shape, monolayer sheets of cells with uniform, small cells, monolayer sheets of cells with small inconspicuous nucleoli.

Insufficient cells to make a diagnosis (ICMD) is characterized when the sample is has less than 10 epithelial cells in the sample.

Previously established cytological assays that can be performed on the cells retrieved from ductal fluid (e.g. washings) or from nipple aspiration of the breast can include e.g. assays described in King et al, *J. Nat'l Cancer Inst* (1983) 71:1115–21, Wrensch et al. (1992) *Am. J. Epidem.* 135: 130–141, Papanicolaou et al, (1958) *Cancer,* 11:377–409 and Goodson W H & King E B, *Chapter 4: Discharges and Secretions of the Nipple,* THE BREAST: COMPREHENSIVE MANAGEMENT OF BENIGN AND MALIGNANT DISEASES (1998) $2^{nd}$ Ed. vol 2, Bland & Kirby eds. W. B. Saunders Co, Philadelphia, Pa. pp. 51–74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073–1080. and King et al, (1983) *JNCI* 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide, staining with a standard cytological stain and evaluation with a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical" "Breast: Guides to Clinical Aspiration Biopsy" (LSBN 0896401596; Masood, *American Society of Clinical Pathology:* November 199S, "Cytopathology of the Breast" ISBN 0891893806; and Feldman P S, *American Society of Clinical Pathology,* November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology) 9(6):713–28, 1993; Masood et al, (Immunohistochemical differentiation of atypical hyperplasia vs. carcinoma in situ of the breast) *Cancer Detection & Prevention.* 16(4): 225–35, 1992; Masood et al, (Cytologic differentiation between proliferative and nonproliferative breast disease in mammographically guided fine-needle aspirates) *Diagnostic Cytopathology.*7(6):581–90, 1991; Masood S., (Occult breast lesions and aspiration biopsy: a new challenge) Diagnostic Cytopathology. 9(6):613–4, 1993; Masood S., (Prognostic factors in breast cancer: use of cytologic preparations) *Diagnostic Cytopathology.* 13(5):388–95, 1995; Novak and Masood, (Nuclear grooves in fine-needle aspiration biopsies of breast lesions: do they have any significance?) *Diagnostic Cytopathology.* 18(5):333–7, 1998; Sidawy et al, (Interobserver variability in the classification of proliferative breast lesions by fine-needle aspiration: results of the Papanicolaou Society of Cytopathology Study) *Diagnostic Cytopathology.* 18(2):150–65, 1998; Masood et al, (Automation in cytology: a survey conducted by the New Technology Task Force, Papanicolaou Society of Cytopathology) *Diagnostic Cytopathology.* 18(1):47–55, 1998; and Frykberg and Masood Copeland E M 3d. Bland K I., (Ductal carcinoma in situ of the breast) *Surgery, Gynecology & Obstetrics* 177(4):425–40, 1993.

In addition to methods of cytologically evaluating ductal epithelial cells retrieved from a human breast, the invention provides a system or kit for making such an evaluation. The system comprises a tool or apparatus for collecting breast duct fluid from a human breast. This tool can comprise items useful for retrieving or collecting ductal fluid from a breast duct or breast nipple such as, for example, a nipple aspirator cup, a breast duct access and fluid and cell retrieval tool, a probe, a tool for administering an anesthetic for ductal access, and/or marking tools for marking an accessed or fluid yielding duct. The system can further also comprise reagents such as the anesthetic, wash fluid for a ductal lavage procedure, dilating probes to enlarge the ductal orifice, dekeratinizing agent for preparing the nipple surface, and other useful items for promoting ductal access and/or fluid retrieval from a breast duct or ducts.

The system can also include a chart or written guidelines for evaluating the ductal epithelial cells in the sample for one or more indicia selected from the group consisting of cell grouping, cell shape, cell size, nuclear size, nuclear shape, presence or absence of nucleoli, nuclear-to-cytoplasmic ratio, vacuoles in the cytoplasm, cytoplasmic shape, cytoplasmic border, presence or absence of anisonucleosis, presence or absence of mitotic figures, nuclear membrane quality, presence of necrotic debris, chromatin distribution, coarseness of chromatin, and the presence or absence of microcalcifications. To accompany these indicia, the system also provides an algorithm for classifying the sample as being normal, atypical (mild or marked) or malignant based on the observed indicia. The algorithm can be a flow or decision chart that indicates at the end of the decisions a diagnosis. Alternatively, or additionally, the algorithm may be a computer program capable of processing the data from a sample to generate a diagnosis.

In any event, the algorithm is capable of classifying the sample as malignant when the sample is characterized by at least some of a loss of cell cohesiveness, loose clusters of epithelial cells, enlarged cells, enlarged nuclei, high nuclear-to-cytoplasmic ratio, increased cytoplasm in some cells, irregular nuclear membranes, clumped chromatin, hyperchromatic chromatin, unevenly dispersed chromatin, enlarged nucleoli, multiple nucleoli, marked variation among the cells of the sample in cell size and nuclear size, necrotic debris, and microcalcifications in background material appearing as dense material with smooth borders and concentric layers or dystrophic and amorphous.

The algorithm is capable of classifying the sample as atypical with marked changes when the sample is characterized by at least some of enlarged ductal epithelial cells, marked nuclear increase in ductal epithelial cells, variation in size and shape of the ductal epithelial cells as compared to normal ductal epithelial cells, abundant cytoplasm in some cells, decreased nuclear-to-cytoplasmic ratios in some cells, coarse chromatin, mild abnormality in chromatin distribution, larger nucleoli than in normal cells, multiple nucleoli, more prominent nucleoli, groups of nuclei that appear to be overlapping, and mitotic figures.

The algorithm is capable of classifying the sample as atypical with mild changes when the sample is characterized by at least some of single ductal cells, cohesive multilayered cells, complex groups of cells, monolayered cells, an increased number of cell layers compared to normal cells, increased overlapping of the cells, nuclear crowding, minimally enlarged cells, moderate increase in nuclear size to within a range from about 12 to about 16 $\mu$m in diameter, slight anisonucleosis in some cells, and presence of nucleoli.

The algorithm is capable of classifying the sample as normal when the sample is characterized by at least some of single cells, monolayer sheets, tight cells clusters usually one or two cell layers thick, small nuclei in a size range from about 8 to about 12 $\mu$m in diameter, high nuclear-to-cytoplasmic ratio depending on the orientation of the cells in clusters, in single cells a columnar shape of cytoplasm, in single cells discreet small vacuoles in the cytoplasm, in single cells discreet cytoplasmic border, cohesive groups of ductal epithelial cells with cells of uniform size and regular round to oval shape, monolayer sheets of cells with uniform, small cells, monolayer sheets of cells with small inconspicuous nucleoli.

The algorithm is capable of classifying the sample as insufficient cells to make a diagnosis (ICMD) when the sample has fewer than 10 epithelial cells are retrieved. Sufficient samples are, for example, in at least one embodiment, samples comprising about 100 ductal epithelial cells, and providing one or more ductal epithelial cell clumps of 10 or more cells per clump.

For both the method of cytological evaluation and the algorithm the following applies: 1) the number of epithelial cells in ductal lavage samples may range from none to several thousand. At least ten epithelial cells are required to designate a sample as adequate. Benign duct cells may be present singly, in monolayer sheets, or in tight clusters or clumps, usually one to two cell layers thick. The cells are small with small nuclei (in a range from about 8 to about 12 $\mu$m in diameter). The nuclear to cytoplasmic ratio may appear to be high depending on the orientation of the cells in clusters. Single benign duct cells are often difficult to identify, often appearing similar to surrounding lymphocytes or histiocytes. Duct cells may be recognized by their nuclear features, the columnar shape of their cytoplasm, or by the presence of discreet small vacuoles in the cytoplasm. The smooth, discreet cytoplasmic border may also help to distinguish duct cells. Benign duct cells are more easily recognized when they occur in groupings. Cohesive groups, as opposed to looser clusters, are more suggestive of epithelial origin. Benign groups are usually one or two cell layers in thickness, and are composed of cells which are uniform in size. The cell nuclei are also uniform in size, and are regularly round to oval in shape. Markers that may be identified in addition to cytological notations, may assist a diagnosis by confirming a cytological reading and or adding additional information to any noteworthy subcategory within the category of benign.

2) The cytological category including atypical epithelial cells, with mild changes, includes duct cells from proliferative conditions including hyperplasia. The cells may occur singly, in cohesive multilayered and complex groups, and in monolayers. The groups may show an increase in the number of cell layers, which can be appreciated by focusing through the groups. Duct groupings also may show increased overlap, with nuclear crowding. The cells may be minimally enlarged, and may show moderate increases in nuclear size, in a range from 12 to 16 $\mu$m in diameter. Slight anisonucleosis may be present among cells in groups. Nucleoli are often present. Markers found in the ductal fluid may assist to identify atypical cells or atypical cells with mild changes, or may confirm such cytological identification.

3) Atypical cells can also include cells with marked changes. More marked changes are often associated with atypical hyperplasia and low grade ductal carcinoma in situ (DCIS) but may also be seen in papillomas and other proliferative conditions. Enlarged duct cells may be present, showing more marked nuclear increase and variation in size and shape. Single cells are enlarged, with the cytoplasm in some cases abundant, nuclear-to-cytoplasmic rations may actually appear decreased. Chromatin may appear coarse, with mild abnormality in distribution. Nucleoli may be larger, multiple, and more prominent. Nuclei in groups may appear to be overlapping. Mitotic figures may be seen. Markers found in the ductal fluid may assist to identify atypical cells with marked changes, or may confirm such cytological identification.

4) Malignant epithelial cells include duct cells from high grade breast carcinoma and exhibit common features of malignancy. More single cells are present, as cell cohesiveness is lost. Loose clusters of epithelial cells are present, along with the more usual tight groups of cells (clumps). Cell and nuclear enlargement may be marked. High nuclear to cytoplasmic ratios may be present in some cases. However, some high grade specimens often have lots of cytoplasm in a portion of the tumor cells, resulting in low or variable nuclear-to-cytoplasmic ratios. Nuclear membranes are often irregular, and chromatin is clumped, hyperchromatic, and unevenly dispersed. Nucleoli are often large and conspicuous and may be multiple. Marked variation among the cells can be seen in terms of cell and nuclear size. Accompanying these changes is often a background of necrotic debris. Microcalcifications may be seen in the background material. These may appear as dense material with smooth borders and concentric layers, or may be dystrophic, amorphous in nature. Markers found in the ductal fluid may assist to identify malignant cells, aspects of malignant indicia, or may confirm such cytological identification. Markers may also help to stage the malignancy or provide other valuable information which might aid in directing a detailed diagnosis and/or treatment options.

Other cytological criteria and processes related to ductal fluid analysis are described in Barret et al, Acta Cytol 1976;20: 174–180; Goodson et al, Discharges and Secretions of the Nipple, THE BREAST: COMPREHENSIVE MANAGEMENT OF BENIGN AND MALIGNANT DISEASES, Second Edition, Vol. 1, Chapter 4, page 1; King et al, Cytometry 1984; 5: 124–130; King et al, A. J. C. P. 1975; 64: 739–748; King et al, A. J. C. P. 1975; 64: 728–738; King et al, Cytopathology of Abnormal Mammary Duct Epithelium, Prevention and Detection of Cancer, Part II, Detection, vol 2 Cancer detection in specific sites, 1976; King et al, J Natl Cancer Inst, 1983; 71: 1115–1121; Kjellgren et al, Acta Cytol 1964; 8: 216–217; Masood et al, The Breast Journal 1999; 5:1–2; Papanicolaou et al, Cancer 1958; 377–409; Petrakis et al, Cancer Epidemiology, Biomarkers and Prevention 1993; 2:3–10; Ringrose et al, Acta Cytol 1966; 10:373–375; Sartorius et al, NCI 1977; 59:1073–1080; Sauter et al, British J. Cancer 1997; 76(4): 494–501; Wrensch et al, Amer J. Epid. 1992; 135: 130–141.

In addition to cytological analysis and evaluation as described above, the ductal epithelial cells may be analyzed for other markers, e.g. protein markers, nucleic acid markers, particles, complexes, or biochemical or molecular markers in the cells or on the cell surfaces or secreted by the cell or for any marker providing evidence of neoplasia. After the fluid is collected the ductal fluid sample can be examined to determine the presence of a marker comprising a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules.

Exemplary markers are described in Masood S., (Prediction of recurrence for advanced breast cancer. Traditional and contemporary pathologic and molecular markers) *Surgical Oncology Clinics of North America.* 4(4) :601–32, 1995; Lopez-Guerrero et al (1999) *J Hematother* 8(1):53–61; Marjumdar and Diamandis (1999) *Br J Cancer* 79(9–10) 1594–602; Balleine et al (1999) *Br J Cancer* 79 (9–10): 1564–71; Houston et al (1999) *Br J Cancer* 79(7–8) :1220–6; Nikolic-Vukosavljevic et al (1998) *Tumori* 84(6): 691–4; Maguire et al (1998) *Int J Biol Markers* 13(3): 139–44; Stearns et al (1998) *Breast Cancer Res Treat* 52(1–3):239–59; Eiriksdottir et al (1998) *Eur J Cancer* 34(13):2076–81, and U.S. Pat. No. 5,169,774. Many known breast cancer markers are discussed and described in readily available medical textbooks on breast cancer. In addition, several markers can be identified and analyzed in the same sample, e.g. Fabian et al 1993 *J. Cellular Biochemistry* 17G:153–16 and Fabian et al 1994 *Breast Cancer Res Treat* 30(3):263–74 looking at estrogen receptor (ER), epidermal growth factor receptor (EGFR), mutant p53, HER-2 neu by immunohistochemistry and aneuploidy by image analysis in fine needle aspirates. Methods described therein can be practiced by analogy to analysis of ductal fluid contents, particularly ductal epithelial cells retrieved by nipple aspiration and/or by ductal lavage techniques.

Chromosomal abnormalities in ductal epithelial cells can also provide information and act as a marker to identify cancer or precancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) *Hereditas* 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J Cellular Biochemistry* 17G: 153–16.

Other breast cancer markers can be detected as described in Springer, G. F. et al, Dao et al, Eds, *Tumor Markers and Their Significance in the Management of Breast Cancer,* pp.47–70, New York; A. R. Liss, 1986. In addition to some markers discussed and/or articles or books cited on breast cancer and breast precancer markers, including markers listed in Porter-Jordan and Lippman, "Overview of the biological markers of breast cancer", Hematology/Oncology Clinics of North America vol. 8 (1):73–100, 1994), the following cancer markers are listed here as exemplary and may be used as well as other markers to analyze the condition of a breast duct, including analysis of the ductal contents (including fluid and cells). Standard assay procedures for identifying the markers can be used, including antibodies or other binding partners, labels, stains, pattern analysis (for cells and cell components), and in general any other chemical or visual identification techniques.

Exemplary markers that are presently being studied by researchers directing their research to breast cancer include, for example, carcinoma embryonic antigen (CEA), prostate specific antigen (PSA) Erb B2 antigen, gross cystic disease fluid protein-15 (GCDFP-15), and lactose dehydrogenase (LDH). For CEA see Imayama et al, *Cancer* 1996, 78(6): 1229–34; Inaji et al, *Cancer* 1987,60(12):3008–13; Mori *Int Conger Seer* 1989, 807:211–8; Inaji, et al, *An To Kagaku Ryoho* 1991, 18(2):313–7; Yayoi, et al *Gan To Kagaku Ryoho* 1994, 21 Suppl 2:133–9; Mori, et al *Jpn J Clin Oncol* 1989,19(4):373–9; Foretova, et al *Proc Annu Meet Am Soc Clin Oncol* 1995,14:A101; and Nishiguchi, et al *Rinsho*

Byori 1992,40(1):67–72. For PSA see Foretova and Garber Lancet 1996,347(9015): 163 1; Sauter et al, *Cancer Epidemiology, Biomarkers & Prevention.* 5(12):967–70, 1996; Sauter and Daly (1996) *Proc Annu Meet Am Assoc Cancer Res* 37:A1458; and Foretova and Garber (1 996) *Proc Annu Meet Am Assoc Cancer Res* 37:A1446. For Erb B2 see Motomura (1995) *Breast Cancer Res and Treat* 33:89–92; and Inaji et al (1993) *Tumour Biol* 14: 271–8. For GCDFP-15 see Petrakis et al (1994) *Proc Annu Meet Am Assoc Cancer Res* 35:A1698. For LDH see Mannello et al (1995) *Cancer* 76:152–4; and Kawamoto (1994) *Cancer* 73:1836–41.

Generally markers can be, for example, a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules. These markers can be detected by detecting an RNA, DNA, protein, polypeptide, or peptide form of a marker. The marker may also or alternatively be an enzyme, a receptor, a protein factor, an inhibitor, or a complex of one or more molecules.

The different categories of markers are tested differently depending on the category and possibly also on the location of the marker in the cell (for example, a cell surface protein might be detected differently than a cytoplasmic or nuclear protein). Typically, assays comprising one or more of binding, coloration, precipitation, affinity column selection, in-situ binding, solution phase binding, nucleic acid probe labeling, protein probe labeling, polypeptide probe labeling, peptide probe labeling, and/or a combination or variation of these processes can be used. Standard procedures for conducting such assays generally (e.g. ELISA, RNA or DNA probe hybridization, and other binding or other detection assays) are described in Sambrook et al., Molecular Cloning: A Laboratory Manual, $2^{nd}$ Ed. (Cold Spring Harbor Press, Cold Spring Harbor, N.Y. 1989).

In general, markers can be categorized nonexclusively, and often in overlapping categories as follows: 1. Markers that are detected or detectable by virtue of protein expression or overexpression (detection may occur, e.g. by immunohistochemistry or in situ hybridization); 2. Markers that are detected or detectable by virtue of mRNA expression or overexpression (detection may occur, e.g. by differential display techniques); 3. Markers that are detected or detectable by virtue of a post translational change in a protein, e.g. a phosphorylation of the protein, a ubiquitination, a farnesylation, methylation, or other modification to the protein that can be detected, e.g. by antibodies specific to the post translational modification. 4. Markers may also be detected based on alteration of a gene, for example methylation of the gene, for example, methylation of the retinoic acid receptor beta-2 gene (RARbeta-2), as described in Widschwendter et al, J Natl Cancer Inst. 2000 92(10) :826–32).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of cytologically evaluatin epithelial cells collected from a human breast duct comprising:

introducing a ductal access tool comprising an elongated internal lumen into the breast duct;

infusing a fluid into the breast duct through said elongated internal lumen of said introduced ductal access tool;

retrieving a sample including ductal epithelial cells from within said duct through said elongated internal lumen of said introduced ductal access tool;

evaluating the ductal epithelial cells in the sample for one or more observed indicia selected from the group consisting of cell grouping, cell shape, cell size, nuclear size, nuclear shape, presence of nucleoli, absence of nucleoli, nuclear-to-cytoplasmic ratio, vacuoles in the cytoplasm, cytoplasmic shape, cytoplasmic border, presence of anisonucleosis, absence of anisonucleosis, presence of mitotic figures, absence of mitotic figures, nuclear membrane quality, presence of necrotic debris, chromatin distribution, coarseness of chromatin, presence of microcalcifications and absence of microcalcifications; and classifying the sample as being normal, atypical or malignant based on the observed indicia.

2. A method as in claim 1, wherein the sample is classified as malignant when the sample is characterized by at least a partial loss of an identifying feature selected from the group consisting of cell cohesiveness, loose clusters of epithelial cells, enlarged cells, enlarged nuclei, high nuclear-to-cytoplasmic ratio, a plurality of cells with increased cytoplasm, irregular nuclear membranes, clumped chromatin, hyperchromatic chromatin, unevenly dispersed chromatin, enlarged nucleoli, multiple nucleoli, abnormal variation among the cells of the sample in cell size and nuclear size, necrotic debris, and microcalcifications in background material appearing as dense material with smooth borders and concentric layers or dystrophic and amorphous.

3. A method as in claim 1, wherein the sample is classified as atypical with marked changes when the sample is characterized by at an identifying feature selected from the group consisting of enlarged ductal epithelial cells, abnormal nuclear increase in ductal epithelial cells, abnormal size and shape of the ductal epithelial cells, abundant cytoplasm in a plurality of cells, decreased nuclear-to-cytoplasmic ratios in a plurality of cells, coarse chromatin, mild abnormality in chromatin distribution, enlarged nucleoli, multiple nucleoli, abnormally prominent nucleoli, nuclei groups that appear to be overlapping, and mitotic figures.

4. A method as in claim 1, wherein the sample is classified as atypical with mild changes when the sample is characterized by at least a portion of an identifying feature selected from the group consisting of single ductal cells, cohesive multilayered cells, complex groups of cells, monolayered cells, an increased number of cell layers compared to normal cells, increased overlapping of the cell, nuclear crowding of cells, minimally enlarged cells, moderate increase in nuclear size to within a range from about 12 to about 16 µm in diameter, anisonucleosis in a plurality of cells, and presence of nucleoli.

5. A method as in claim 1, wherein the sample is classified as normal when the sample is characterized by at least an identifying feature selected from the group consisting of single cells, monolayer sheets, tight cells clusters, small nuclei in a size range from about 8 to about 12 µm in diameter, high nuclear-to-cytoplasmic ratio depending on the orientation of the cells in clusters, single cells having a columnar shaped cytoplasm, single cells with cytoplasms having discreet small vacuoles, single cells with discreet cytoplasmic borders, cohesive groups of ductal epithelial cells with cells of uniform size and normal round to oval shapes, monolayer sheets of cells with uniform, small cells, and monolayer sheets of cells with small inconspicuous nucleoli.

6. A method as in claim 1, wherein the sample is classified as insufficient cells to make a diagnosis (ICMD) when the sample includes less than 10 cells.

7. A method as in any of claims 1–6 wherein the method is repeated for a plurality of ducts in a breast.

8. A method as in claim 1, wherein the fluid infused is in a range from about 2 ml to about 100 ml during a total lavage procedure on a single breast duct.

9. A method as in claim 1, wherein the fluid sample retrieved is in a range from about 2 ml to about 30 ml of wash fluid mixed with cellular material.

10. A method as in claim 1, wherein the cells retrieved comprise excess of about 500 cells.

11. A method as in claim 1, wherein the cells retrieved comprise an amount in a range from about 500 cells to about 40,000 cells from a single breast duct.

12. A method as in claim 1, wherein the sample retrieved comprises at least one cluster of cells including 10 or more ductal epithelial cells.

13. A method as in claim 1 further comprising a step of:
examining the ductal fluid sample to determine the presence of a marker selected from the group consisting of a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, and a complex of a plurality of molecules.

14. A method of cytological evaluating epithelial cells collected from a human breast duct comprising:
providing a ductal fluid sample comprising at least 500 ductal epithelial cells from a duct of a breast of a patient;
evaluating the ductal epithelial cells in the sample for one or more observed indicia selected from the group consisting of cell grouping, cell shape, cell size, nuclear size, nuclear shape, presence of nucleoli, absence of nucleoli, nuclear-to-cytoplasmic ratio, vacuoles in the cytoplasm, cytoplasmic shape, cytoplasmic border, presence of anisonucleosis, absence of anisonucleosis, presence of mitotic figures, absence of mitotic figures, nuclear membrane quality, presence of necrotic debris, chromatin distribution, coarseness of chromatin, presence of microcalcifications and absence of microcalcifications; and
classifying the sample as being normal, atypical or maligant based on the observed indicia.

15. A method of cytologically evaluating epithelial cells collected from a human breast duct comprising:
providing a ductal fluid sample comprising at least 100 ductal pithelial cells from a duct of a breast of a patient and at least one cell clump comprising a least 10 cells from the duct;
evaluating the ductal epithelial cells in the sample for one or more observed indicia selected from the group consisting of cell grouping, cell shape, cell size, nuclear size, nuclear shape, presence of nucleoli, absence of nucleoli, nuclear-to-cytoplasmic ratio, vacuoles in the cytoplasm, cytoplasmic shape, cytoplasmic border, presence of anisonucleosis, absence of anisonucleosis, presence of mitotic figures, absence of mitotic figures, nuclear membrane quality, presence of necrotic debris, chromatin distribution, coarseness of chromatin, presence of microcalcifications and absence of microcalcifications; and
classifying the sample as being normal, atypical or malignant based on the observed indicia.

16. A method of cytologically evaluating epithelial cells collected from a human breast duct comprising:
introducing a ductal access tool comprising an elongated internal lumen into the breast duct;
infusing a fluid into the breast duct through said elongated internal lumen of said introduced ductal access tool;
retrieving a sample from within said duct through said elongated internal lumen of said introduced ductal access tool, said sample including at least one hundred ductal epithelial cells;
evaluating the ductal epithelial cells in the retrieved sample for one or more observed indicia selected from the group consisting of cell grouping, cell shape, cell size, nuclear size, nuclear shape, presence of nucleoli, absence of nucleoli, nuclear-to-cytoplasmic ratio, vacuoles in the cytoplasm, cytoplasmic shape, cytoplasmic border, presence of anisonucleosis, absence of anisonucleosis, presence of mitotic figures, absence of mitotic figures, nuclear membrane quality, presence of necrotic debris, chromatin distribution, coarseness of chromatin, presence of microcalcifications and absence of microcalcifications; and
classifying the cells of the retrieved sample as being normal, atypical or malignant based on the observed indicia.

17. A method as in claim 16, therein cells of the sample are classified as malignant when the sample is characterized by at least a partial loss of an identifying feature selected from the group consisting of cell cohesiveness, loose clusters of epithelial cells, enlarged cells, enlarged nuclei, high nuclear-to-cytoplasmic ratio, a plurality of cells with increased cytoplasm, irregular nuclear membranes, clumped chromatin, hyperchromatic chromatin, unevenly dispersed chromatin, enlarged nucleoli, multiple nucleoli, abnormal variation among the cells of the sample in cell size and nuclear size, necrotic debris, and microcalcifications in background material appearing as dense material with smooth borders and concentric layers or dystrophic and amorphous.

18. A method as in claim 16, therein cells of the sample are classified as atypical with marked changes when the sample is characterized by at least an identifying feature selected from the group consisting of enlarged ductal epithelial cells, abnormal nuclear increase in ductal epithelial cells, abnormal size and shape of the ductal epithelial cells, abundant cytoplasm in a plurality of cells, decreased nuclear-to-cytoplasmic ratios in a plurality of cells, coarse chromatin, mild abnormality in chromatin distribution, enlarged nucleoli, multiple nucleoli, abnormally prominent nucleoli, nuclei groups that appear to be overlapping, and mitotic figures.

19. A method as in claim 16, wherein the sample is classified as atypical with mild changes when the sample is characterized by at least a portion of an identifying feature selected from the group consisting of single ductal cells, cohesive multilayered cells, complex groups of cells, monolayered cells, an increased number of cell layers compared to normal cells, increased overlapping of the cells, nuclear crowding of cells, minimally enlarged cells, moderate increase in nuclear size to within a range from about 12 to about 16 µm in diameter, anisonucleosis in a plurality of cells, and presence of nucleoli.

20. A method as in claim 16, wherein the sample is classified as normal when the sample is characterized by at least an identifying feature selected from the group consisting of single cells, monolayer sheets, tight cells clusters, small nuclei in a size range from about 8 to about 12 µm in diameter, high nuclear-to-cytoplasmic ratio depending on the orientation of the cells in clusters, single cells having a colunmar shaped cytoplasm, single cells with cytoplasms having discreet small vacuoles, single cells with discreet cytoplasmic borders, cohesive groups of ductal epithelial cells with cells of uniform size and normal round to oval shapes, monolayer sheets of cells with uniform, small cells, and monolayer sheets of cells with small inconspicuous nucleoli.

21. A method as in claim 16, wherein the sample comprises at least about 500 cells.

22. A method as in claim 16, wherein the sample retrieved comprises at least one cluster of cells including 10 or more ductal epithelial cells.

* * * * *